United States Patent [19]
Jarvik

[11] 3,985,138
[45] Oct. 12, 1976

[54] PREFORMED LIGATURES FOR BLEEDERS AND METHODS OF APPLYING SUCH LIGATURES

[76] Inventor: Robert K. Jarvik, 5974 Holladay Blvd., Salt Lake City, Utah 84121

[22] Filed: Oct. 10, 1974

[21] Appl. No.: 513,929

Related U.S. Application Data

[60] Continuation-in-part of Ser. No. 283,773, Aug. 25, 1972, Pat. No. 3,841,521, which is a division of Ser. No. 64,161, Aug. 17, 1970, Pat. No. 3,687,138.

[52] U.S. Cl. .............................. 128/326; 128/335.5
[51] Int. Cl.$^2$ ................. A61B 17/12; A61B 17/04; A61L 17/00
[58] Field of Search ............ 24/30.5 P, 16 PB, 260; 128/326, 335.5

[56] References Cited
UNITED STATES PATENTS

| | | | |
|---|---|---|---|
| 1,400,653 | 12/1921 | Barbour | 128/326 UX |
| 1,691,386 | 11/1928 | Fisher | 128/326 |
| 3,224,056 | 12/1965 | Joffe | 24/16 PB |
| 3,600,027 | 8/1971 | Noland et al. | 24/16 PB X |
| 3,744,096 | 7/1973 | Kok | 24/16 PB |

FOREIGN PATENTS OR APPLICATIONS

| | | | |
|---|---|---|---|
| 1,281,537 | 12/1961 | France | 24/16 PB |
| 1,471,561 | 1/1967 | France | 24/30.5 P |

*Primary Examiner*—Channing L. Pace
*Attorney, Agent, or Firm*—Mattern, Ware, Davis & Stoltz

[57] ABSTRACT

A preformed ligature comprises a loop, loop forming closure and an extension which may be pulled to close the loop about a bleeder. One preformed ligature according to the invention is formed of a continuous loop of gut or synthetic suture material tied into a slip knot to form the closure and the extension is the second loop thus formed therein which may be pulled by means of a hook. Another preformed dual loop ligature is formed of a continuous loop of suture material and a narrow enveloping closure. The loop preferably has a ratchet-like surface and the closure a cooperating pawl-like surface to provide a ligature loop that may only slip one way.

The loop and the closure, in one embodiment, are each provided with an extension ending in a finger engaging loop. These are grasped and pulled to close the closure around a bleeder or the like. In another embodiment, the loop is provided with an extension and a finger loop and the closure is pushed closed by means of an eyelet mounted on a stick.

In alternative embodiments, the closure is smooth on the inside and formed of material having elastic memory. The normal shape of the closure is round and, when in this shape, its inner edges engage the ratchet-like pawls of the loop. Under axial pressure the closure may be pushed along the pawls in one direction to close one end of the loop about a bleeder or the like.

The loops of the hand applied ligatures are large enough to be slipped over a hemostat.

8 Claims, 41 Drawing Figures

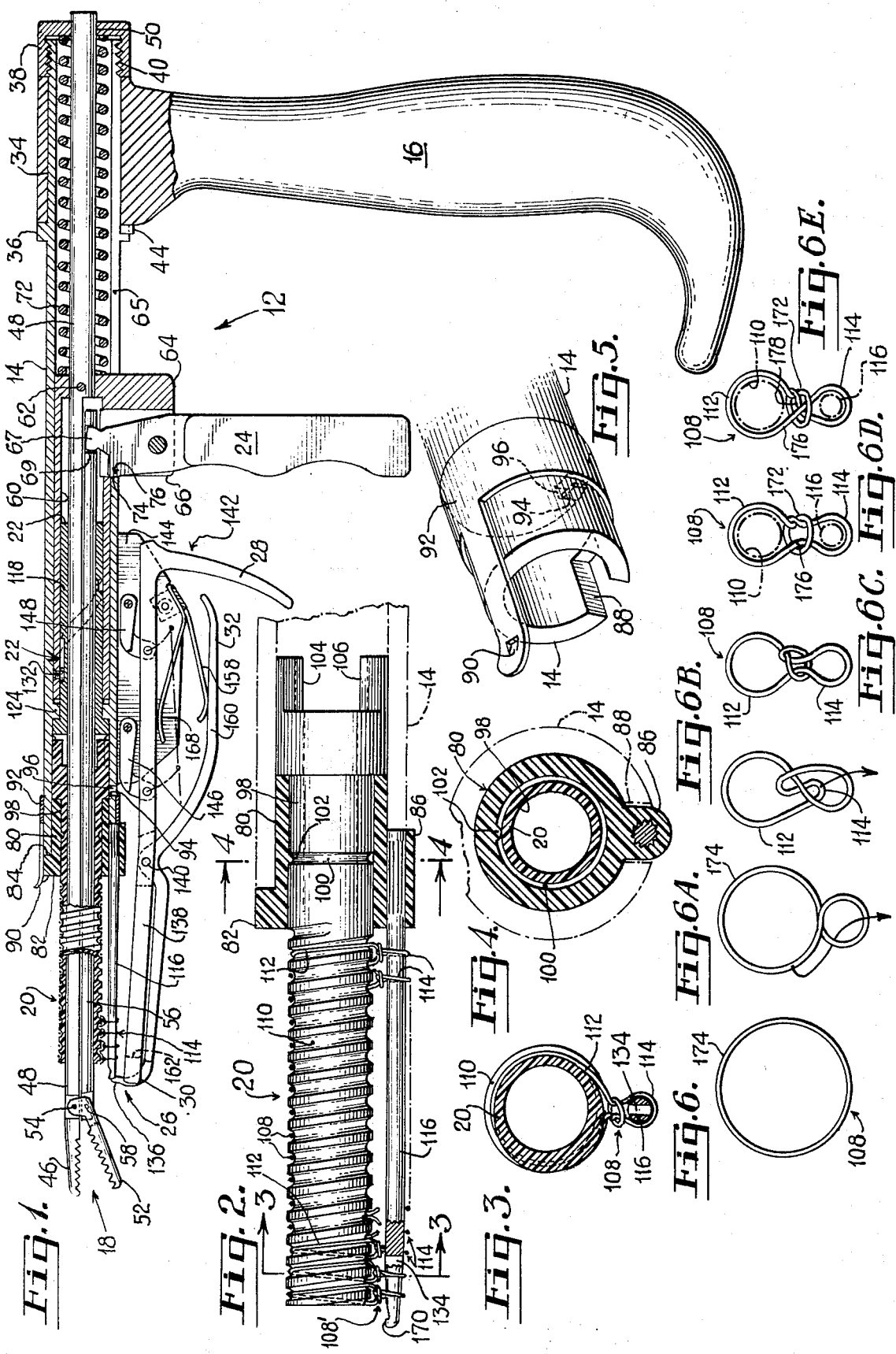

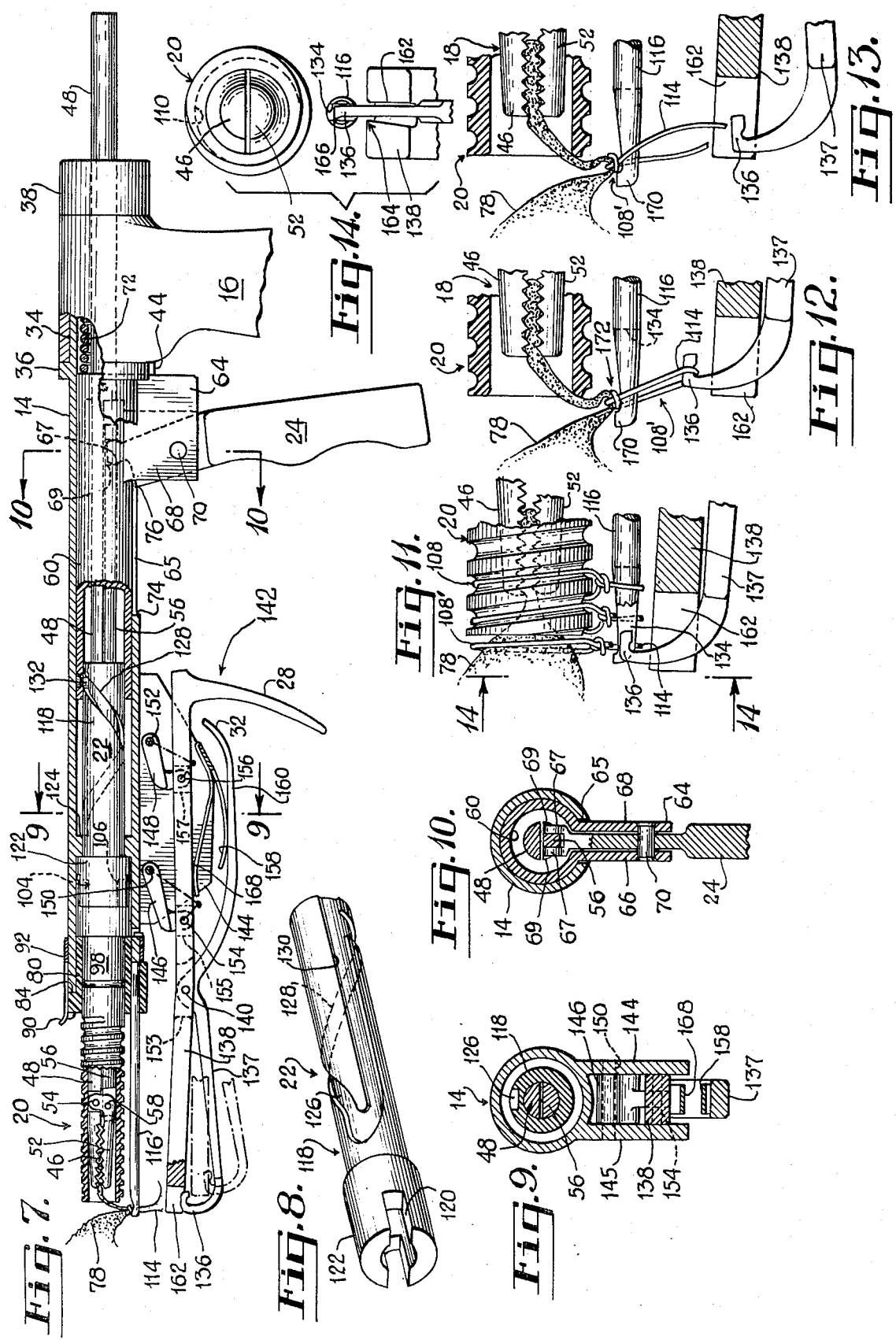

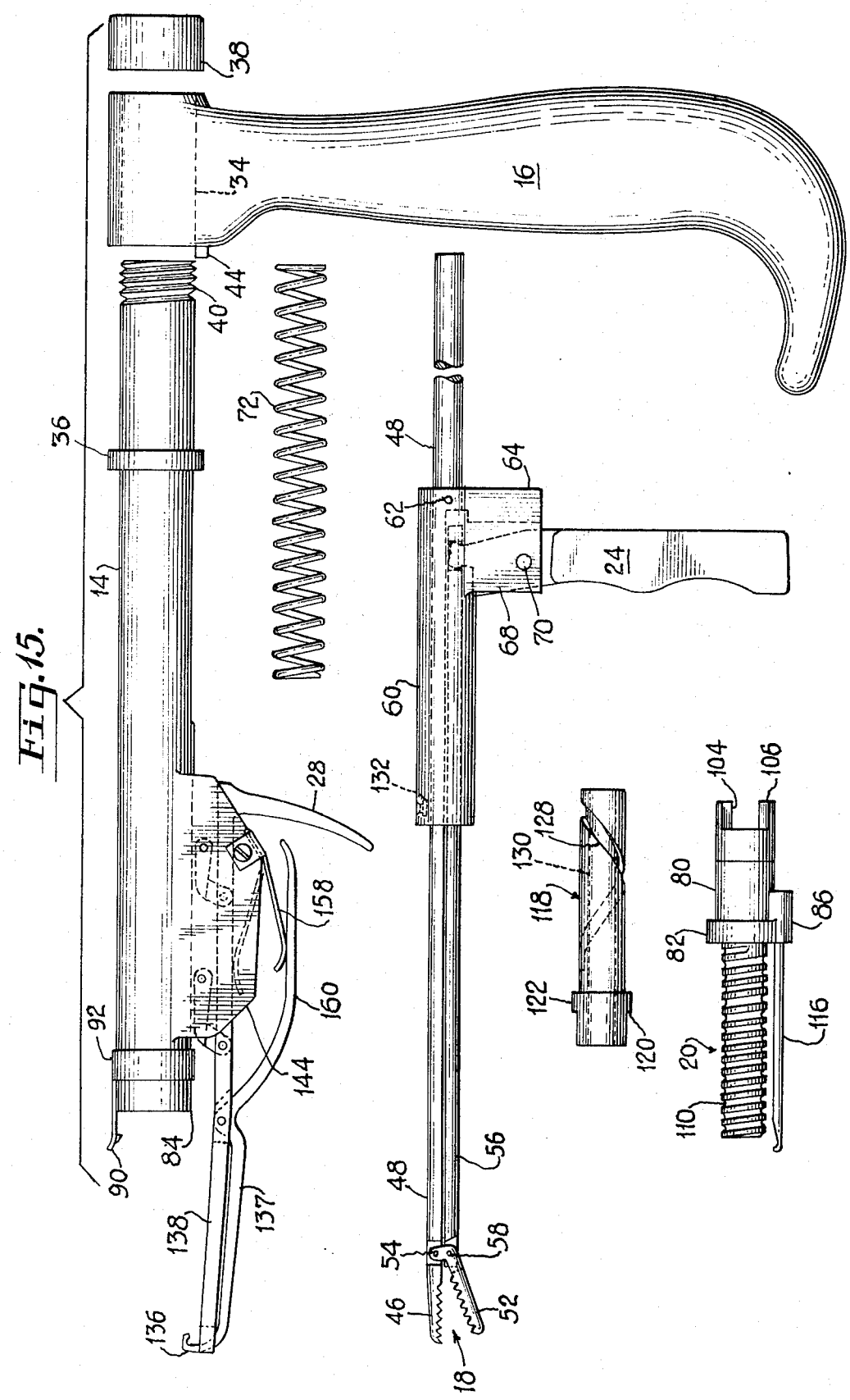

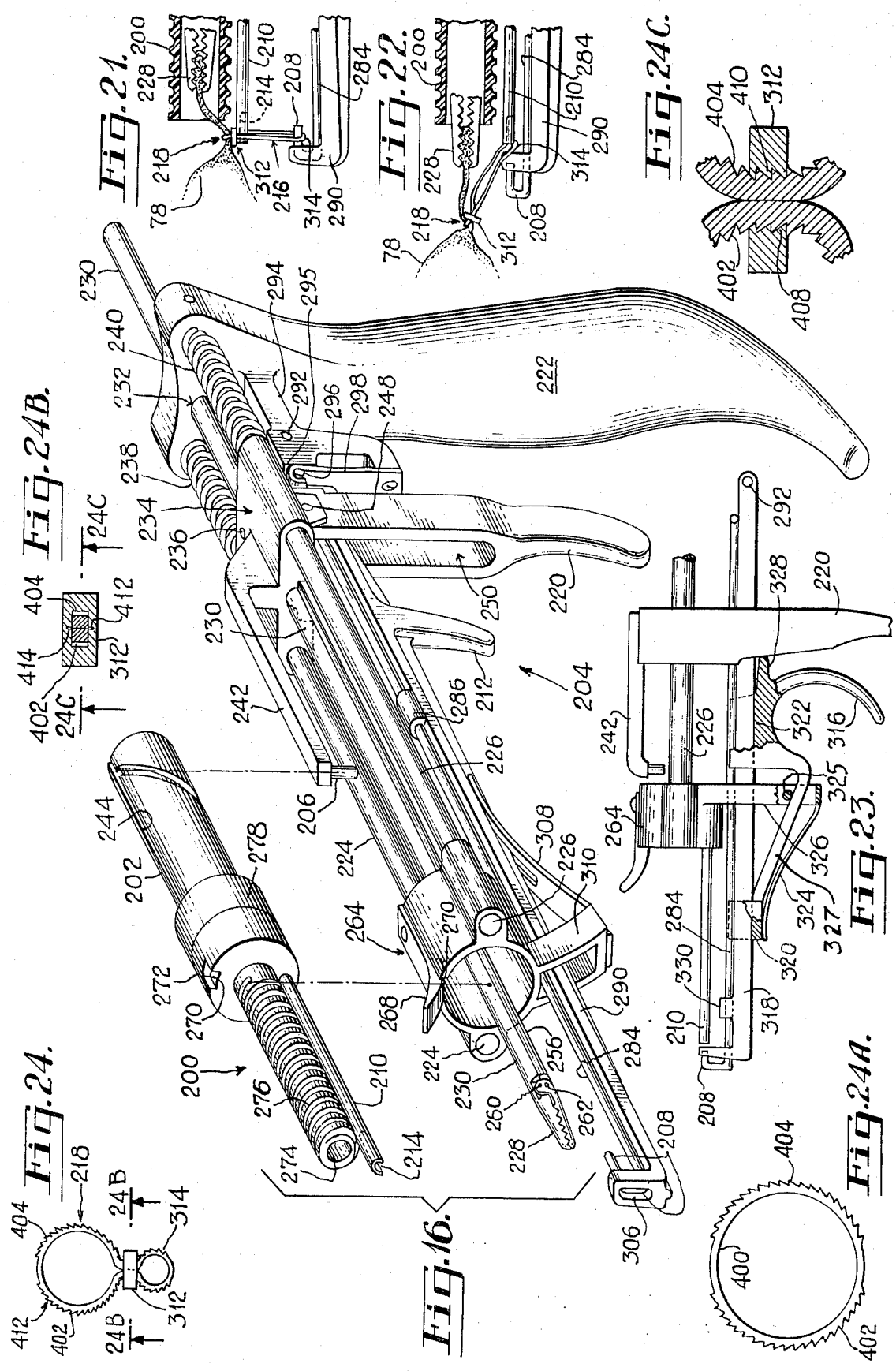

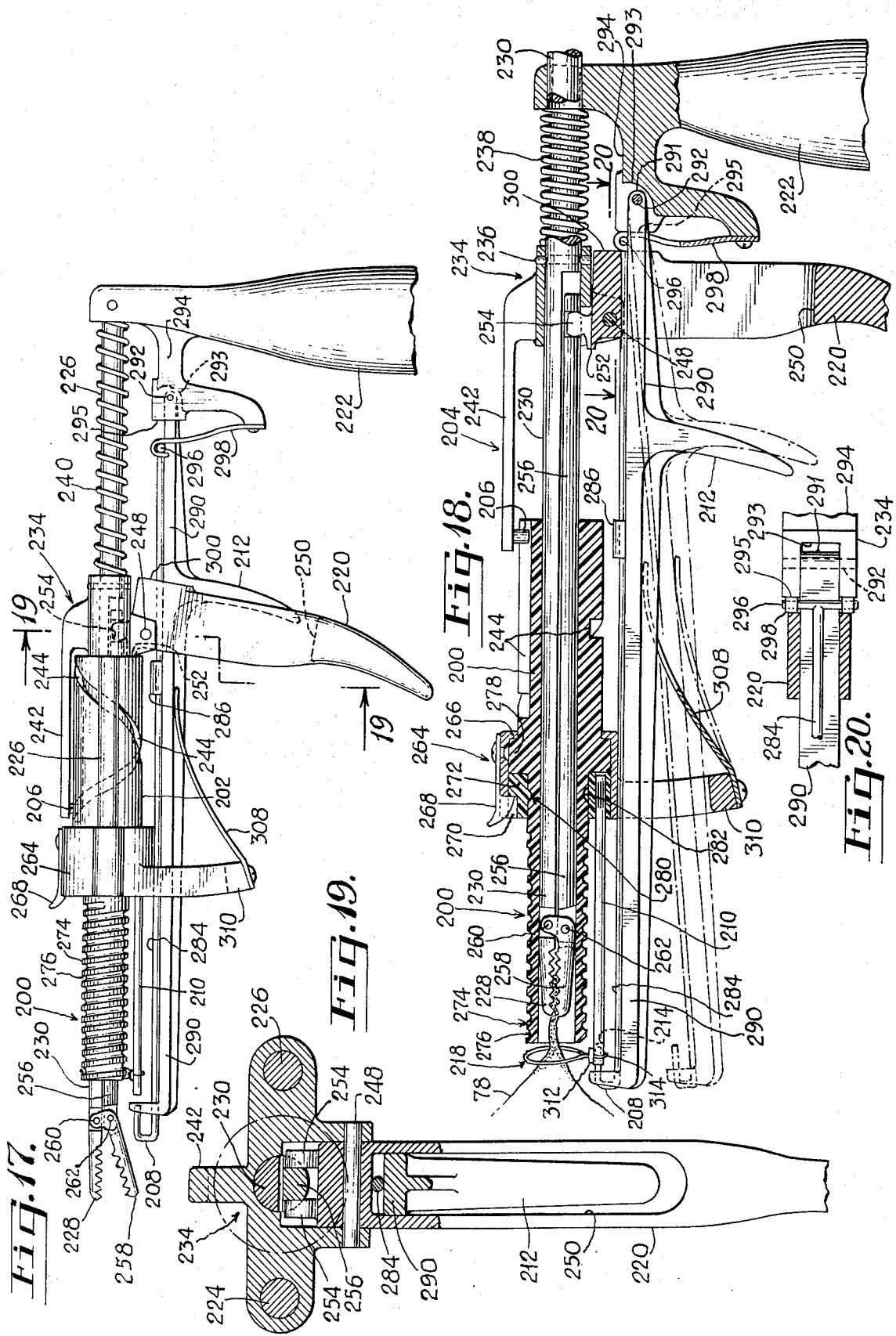

FIG. 25
FIG. 26
FIG. 27
FIG. 28
FIG. 29
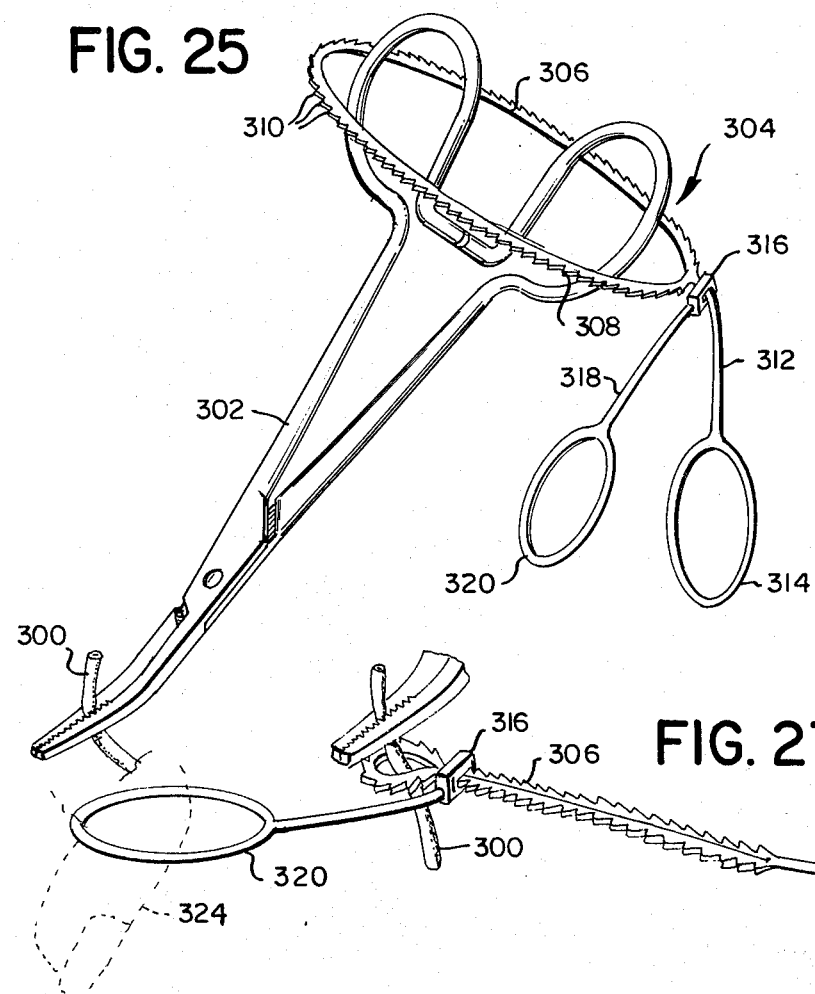
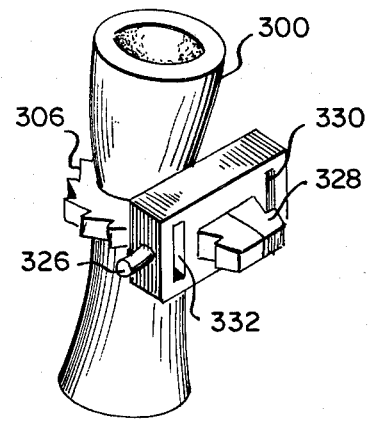
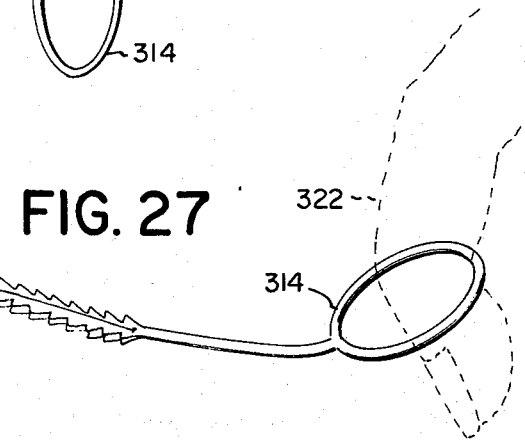
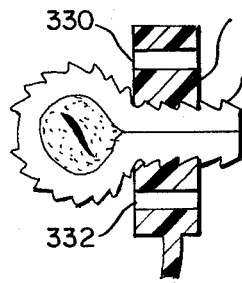
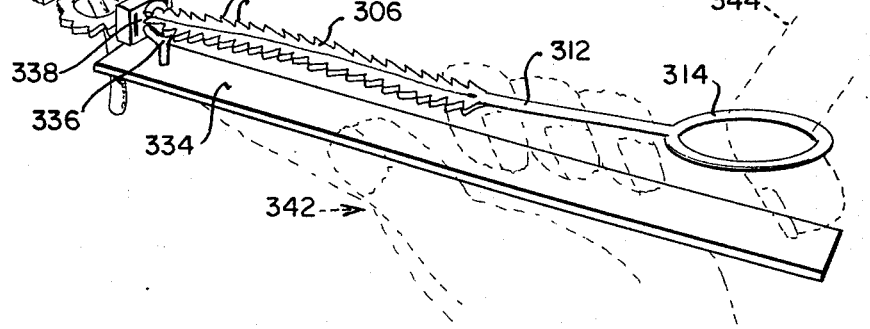

PREFORMED LIGATURES FOR BLEEDERS AND METHODS OF APPLYING SUCH LIGATURES

RELATED APPLICATIONS

This application is a continuation-in-part of my copending application Ser. No. 283,773 filed Aug. 25, 1972, issued as U.S. Pat. No. 3,841,521 on Oct. 15, 1974. My application Ser. No. 283,773 was a divisional of my application Ser. No. 64,161 filed Aug. 18, 1970, now U.S. Pat. No. 3,687,138 issued Aug. 29, 1972.

SUMMARY OF THE INVENTION

This invention relates to preformed ligatures for bleeders and methods of applying such ligatures. More particularly, it relates to the rapid and repeated ligation of so-called bleeders in surgical procedures.

After a surgeon has made an incision, it is necessary to clamp the tissue wherever blood is being lost due to the cutting of blood vessels. The usual technique is to clamp each so-called bleeder with a hemostat (locking dog nosed pliers) as soon after the vessel is severed as possible. This controls the loss of blood until a ligature can be tied around the vessel. As many as twenty or more bleeders may be clamped by as many hemostats in common surgical procedures before they are tied. Thus, a single operation often requires the use of a large number of hemostats. These are handed to the surgeon and his assistants, one at a time, by the scrub nurse.

The surgical field often becomes cluttered with hemostats, which interfere with the surgeon's view and hinder the convenient application of additional hemostats. However, good surgical practice requires the application of hemostats to all bleeders before any are tied.

The tying process requires one hand to hold the hemostat and two hands to pass the suture material around the hemostat and to form the ligature by tying a knot. This procedure thus requires two people. In addition, the ligatures must be cut and the excess suture material removed from the incision. The used hemostats must be handed to the scrub nurse and be readied for reuse. Thus, this entire technique for the achievement of hemostasis requires the coordination and teamwork of at least three people. The speed with which the bleeders may be tied off is often the determined factor in the time required for the opening stages of many surgical operations.

Many instruments have been disclosed in the prior art for ligating bleeders. However, none of these have come into general use, due to inherent deficiencies. Instruments such as disclosed in U.S. Pat. Nos. 3,033,204, 3,040,747, and 3,169,526, issued to E. C. Wood; U.S. Pat. No. 2,268,755, issued to S. F. Li; and U.S. Pat. No. 1,625,602, issued to H. G. Gould et al, have beed designed for aiding the surgeon in applying a single pretied length of suture material to a bleeder. Other instruments, such as that disclosed in U.S. Pat. No. 2,371,082, issued to F. Vistreich are designed to apply a single collar of resilient material to a deep bleeder. However, these instruments, since they apply only one ligature at a time after which another preformed ligature must be affixed to the instrument before it can then be applied to the next bleeder, do not materially reduce the amount of time or effort required in a surgical procedure. Other more complex instruments, such as disclosed in U.S. Pat. Nos. 2,898,915 and 2,898,916, issued to K. Kammer, have been devised for automatically tying a successive plurality of ligatures from a spool of suture material. However, these instruments are complex, are difficult to load with the suture material, and, being complicated, are hard to disassemble and sterilize. None of the above prior art instruments have come into general use.

What is needed is an instrument which will rapidly and repeatedly clamp and ligate bleeders; an instrument that can be operated with one hand; an instrument which does not leave any excess material, such as cut ends in the incision; and instrument which may be reloaded by means of a cartridge with a plurality of pretied ligatures repeatedly during an operation; and an instrument which is easy to disassemble and sterilize.

There is also a need for single preformed ligatures that may be applied quickly and easily to inaccessible sites. A prior art ligature of this type comprises a length of plastic suture material threaded through a button to form a loop that may be closed by threading the end of the suture material through a soda straw and pulling on it. This ligature is of course hard to assemble and costly.

OBJECTS OF THE INVENTION

It is therefore an object of the invention to improve that art of surgery.

Another object of the invention is to provide for rapid ligation of a plurality of bleeders.

Still another object of the invention is to provide pretied ligatures for facilitating the above objects.

Yet still another object of the invention is to provide means both manual and automatic for applying such ligatures.

Another object of the invention is to provide ligatures of the above character that are easily manufactured and assembled at low cost.

A further object of the invention is to provide an instrument for applying a plurality of ligatures of the above character.

Another object of the invention is to provide an instrument of the above character which may be operated by one hand.

A further object of the invention is to provide an instrument of the above character which leaves no excess material or cut ends on the sutures in the body which have to be removed by the surgeon.

Still another object of the invention is to provide an instrument of the above character which is convenient to sterilize.

Yet another object of the invention is to provide an instrument of the above character which does not require lubrication.

Still another object of the invention is to provide an instrument of the above character employing a replaceable cartridge or carrier for a plurality of pretied ligatures of the above character.

A further object of the invention is to provide a cartridge of the above character which is disposable.

A still further object of the invention is to provide an instrument and ligatures of the above character which ligatures can be affixed to bleeders with varying tension according to the size of the vessel and type of tissue in which it occurs.

Still another object of the invention is to provide an instrument, cartridge and preformed ligatures of the above character which may be mass produced at low cost, and convenient to use and require little or no servicing.

Other objects of the invention will in part be obvious and will in part appear hereinafter.

The invention accordingly comprises articles of manufacture possessing the features, properties and the relations of elements which will be exemplified in the articles hereinafter described, and apparatus comprising the features of construction, combinations of elements and arrangements of parts which will be exemplified in the constructions hereinafter set forth. The scope of the invention is indicated in the claims.

THE DRAWINGS

For a fuller understanding of the nature and objects of the invention, reference should be had to the following detailed description taken in connection with the accompanying drawings in which:

FIG. 1 is a side view, partially in cross section, of a repeating ligature gun according to the invention;

FIG. 2 is an enlarged fragmentary side view, partially in cross section, of the disposable multiple ligature-bearing cartridge of the repeating ligature gun of FIG. 1;

FIG. 3 is a cross sectional view taken along the lines 3—3 of FIG. 2; FIG. 4 is a cross sectional view taken along the lines 4—4 of FIG. 2;

FIG. 5 is an enlarged fragmentary perspective view of the cartridge-engaging portion of the ligature gun of FIG. 1;

FIG. 6 is a top view of a continuous loop of suture material which may be formed into a pretied ligature according to the invention.

Figure 31:
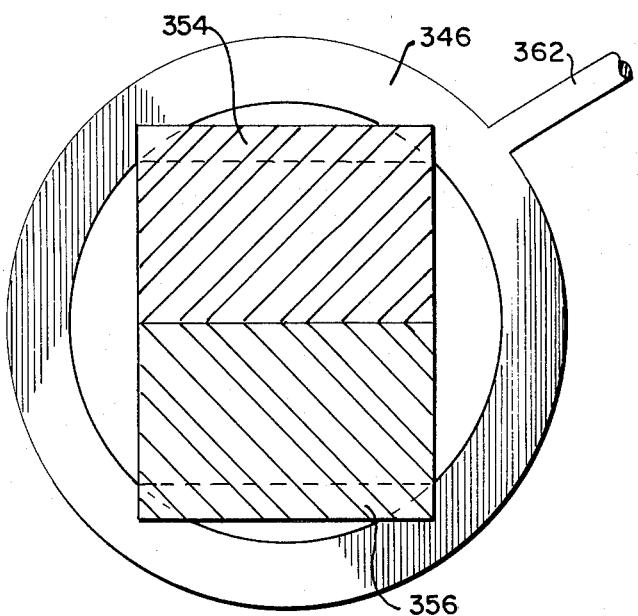
Figure 30:
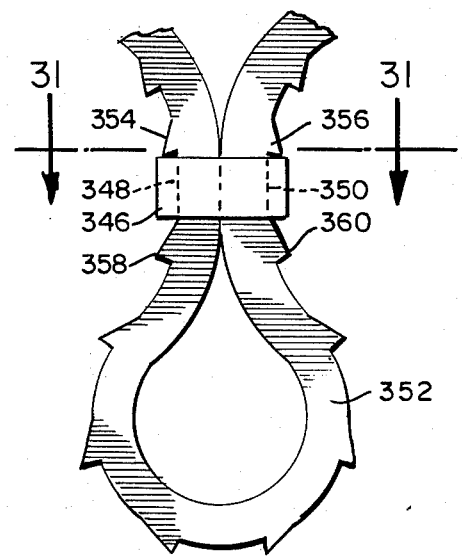
Figure 33:
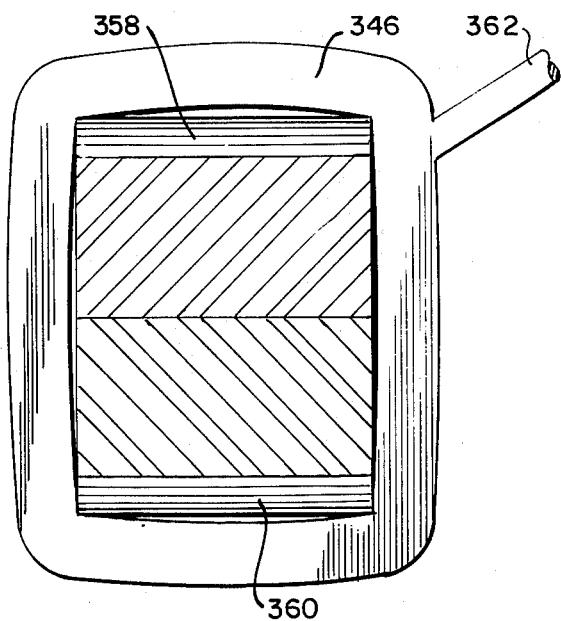
Figure 32:
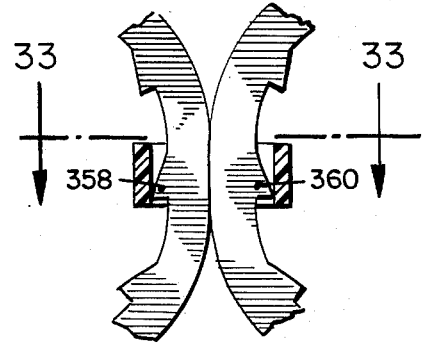

FIGS. 6A, 6B, 6C, 6D, and 6E illustrate the manner in which the continuous loop suture of FIG. 6 may be formed into a pretied ligature according to the invention;

FIG. 7 is a side view, partially cut away and partially in cross section and similar to FIG. 1, of the repeating ligature gun of FIG. 1;

FIG. 8 is an enlarged perspective view of a cam in the ligature gun of FIG. 1;

FIG. 9 is an enlarged cross sectional view taken along the lines 9—9 of FIG. 7;

FIG. 10 is an enlarged cross sectional view taken along the lines 10—10 of FIG. 7;

FIGS. 11, 12 and 13 are enlarged fragmentary side views of the tissue engaging end of the repeating ligature gun of FIG. 1, illustrating the application of a ligature as shown in FIG. 6 to a bleeder;

FIG. 14 is a front view taken along the lines 14—14 of FIG. 11 with the bleeder removed;

FIG. 15 is a side view of the elments of the repeating ligature gun of FIG. 1 disassembled for cleaning and sterilization;

FIG. 16 is a perspective view of another embodiment of the repeating ligature gun of the present invention;

FIG. 17 is a side view of the repeating ligature gun of FIG. 16;

FIG. 18 is an enlarged fragmentary side view, partially in cross section, of the repeating ligature gun of FIG. 16;

FIG. 19 is a fragmentary enlarged cross sectional view taken along the lines 19—19 of FIG. 17;

FIG. 20 is a fragmentary cross sectional view taken along the lines 20—20 of FIG. 18;

FIGS. 21 and 22 are enlarged fragmentary side views of the tissue engaging end of the repeating ligature gun of FIG. 17, illustrating the application of a ligature as shown in FIG. 24;

FIG. 23 is a fragmentary side view, partially in cross section of a modified of the repeating ligature gun of FIG. 15;

FIG. 24 is a top view of a preformed ligature according to the invention;

FIG. 24A is a top view of a portion of the ligature of FIG. 24;

FIG. 24B is a cross-sectional view taken along the lines of 24B—24B of FIG. 24;

FIG. 24C is a cross-sectional view taken along the lines 24C–24C of FIG. 24B;

FIG. 25 is a perspective view of a hand applied single ligature similar to the ligature of FIG. 4 according to my invention, being passed over a hemostat for application to a clamped bleeder;

FIG. 26 is an enlarged view showing the ligature of FIG. 25 applied to a bleeder;

FIG. 27 is a view similar to FIG. 25 showing the method of closing the loop of the ligature by pulling the two finger loops thereof;

FIG. 28 is a cross-sectional view of the ligature and blood vessel shown in FIG. 26;

FIG. 29 is a perspective view of an alternative method of applying a slightly modified ligature;

FIG. 30 is an enlarged view partially cut away of an alternative form of ligature and closure;

FIG. 31 is an enlarged cross-sectional view taken along the line 31—31 of FIG. 30;

FIG. 32 is a view partially cut away similar to FIG. 30 of the same ligature as shown in FIG. 30 with the closure in a different position; and FIG. 33 is an enlarged cross-sectional view taken along the line 33—33 of FIG. 32.

GENERAL DESCRIPTION

In general, preformed ligatures according to the invention comprise a continuous loop of suture material, that has been tied into a slip knot as illustrated in FIG. 6D or which is provided with a tight-fitting collar as illustrated in FIG. 24 to form the pretied ligature into two loops, one of which may be expanded to contract the other, the contracting loop becoming the actual ligature.

The preformed ligature loop may be injection molded of suitable plastic material and is provided with a plurality of pawls on its outer surface. A resilient collar fitted about the loop also may be injected molded. Several embodiments of the invention are provided with a cooperating pawl-like inner surface. Thus, as in a ratchet, the collar or closure may be pushed in one direction to close one end of the loop but may not be pushed in the other direction to open the same end. Alternatively, the collar or closure may be formed of plastic material having an elastic memory which tends to form itself into a circle. Such as closure when so formed, may not be moved with respect to the ratchet-like teeth on the outer surface of the ligature loop however, under axial pressure, the collar or closure deforms and may be slipped in one direction along the ratchet-like teeth.

Such preformed ligatures may be applied to bleeders manually one at a time by providing the loop with an elongated extension ending in a finger engaging loop and also providing the collar or closure with a similar elongated extension ending in a finger engaging loop. The ligature loop is passed over the bleeder, and the two finger engaging loops are grasped by opposite hands and pulled to close one end of the ligature loop about the bleeder. Excess material is then cut away by means of scissors or the like leaving the closure and the small closed end of the ligature loop about the bleeder.

Alternatively, the closure need not be provided with an extension and finger engaging loop. An elongated stick or the like having an eyelet mounted at one end thereof may be used so that the eyelet can be pushed against the closure to close the bleeder engaging portion of the ligature loop.

Hand applied ligature loops are preferably formed large enough to pass over a hemostat for application to a previously clamped bleeder.

A plurality of such ligatures are mounted on a ligature carrier cartridge, as illustrated in FIGS. 2 and 16. The barrel of the carrier is provided with a helical track about one turn of which one of the loops of each of the preformed ligatures is engaged. The other loop of each ligature is engaged about an elongated pin slightly displaced from and parallel to the helical track.

A cam is provided for rotating the helical track with respect to the elongated pin. The cam may be a portion of the ligature gun, as illustrated in FIGS. 7 and 8, or may be a portion of the cartridge, as illustrated in FIG. 16.

The cartridge has an axial bore through which, when the cartridge is mounted on the ligature gun, gripper jaws may be retracted to pull a bleeder into the end of the cartridge.

The repeating ligature guns of the invention are provided with means for rotating the helical track one revolution each time the jaws are retracted into the end of the cartridge. Preferably a single trigger causes the jaws to grip the bleeder, draw the bleeder into the cartridge, and to rotate the helical track to allow the ligature to engage the bleeder. Another trigger is provided which operates a hook, which thereafter engages the second loop of the preformed ligature and pulls the same such that the slip knot or collar thereof is caused to move towards the bleeder and the loop about the bleeder to close therearound, forming the ligature.

In one embodiment of the invention, the open loop not engaging the bleeder is then cut to release it from the gun. In another embodiment of the invention, it is not cut.

All automatic instruments of the invention provide for the application of a large plurality of ligatures before it is necessary to reload the instrument and also provide for convenient reloading of the instrument so a single instrument may be used throughout the course of a single operation.

SPECIFIC DESCRIPTION

More particularly, referring to FIG. 1, a repeating ligature gun 12 according to the invention comprises an elongated outer barrel 14; a handle 16; tissue-gripping jaws, generally indicated at 18; a ligature cartridge, generally indicated at 20; a cam assembly, generally indicated at 22, for rotating the ligature cartridge 20; a trigger 24 for closing the jaws 18, for causing the jaws to retract within the cartridge 20, and for rotating the cartridge 20 by means of the cam mechanism 22; a hook mechanism, generally indicated at 26; a trigger 28 for operating the same; a cutter 30; and a trigger 32 for operating the cutter.

As illustrated in FIGS. 1, 7, and 15, the handle 16 is provided with a bore 34 for engaging the barrel 14. The handle 16 is clamped onto the barrel 14 between a circumferential annular stop 36 and an end cap 38 threaded onto the barrel 14 at threads 40. The lowermost portion of the barrel 14 is slotted as at 65 and is engaged by a key 44 formed on the handle 16 to prevent relative rotation of the barrel 14 with respect to the handle 16 and to provide a stop for the stroke of extension 64 described below.

Referring to FIG. 1, the upper jaw 46 of the gripping jaws 18 is integrally formed on an elongated rod 48 which passes through the entire length of the instrument. A bore 50 is formed in the end cap to support one end of the rod 48, another position being supported by pin 62 as described below. The lower jaw 52 is pivoted to rod 48 at pivot 54. The forward end of rod 48 is half round so that a second half round rod 56 can actuate lower jaw 52 by means of its attachment at pivot 58.

Still referring to FIG. 1, the elongated upper jaw rod 48 is mounted to an inner barrel assembly 60 at pin 62.

Referring to FIGS. 1, 7, and 10, inner barrel assembly 60 is provided with an extension 64 which passes through slot 65 provided in outer barrel 14. Extension 64 is provided with a pair of depending extensions arms 66 and 68 best seen in FIG. 10. Trigger 24 is mounted for pivotal rotation about a pivot 70, extending between extension arms 66 and 68. Trigger 24 is provided with a pair of wishbone-like extensions 67—67 which engage slots 69—69 in the lower half-round jaw actuating rod 56.

Referring to FIG. 1, inner barrel assembly 60 is biased forward by means of a compression spring 72 until extension arms 66 and 68 come to rest against the forward end 74 of slot 65. In this relaxed position, the forward edge 76 of trigger 24 also comes into contact with the slot edge 74 and the trigger is biased clockwise to open jaws 18.

When the trigger 24 is initially pulled towards the handle 16, its initial counterclockwise rotation pushes lower jaw actuating rod 56 forward, rotating lower jaw 52 clockwise as seen in FIG. 1, thus, closing the jaws 18. Further pulling of the trigger 24 causes the inner barrel assembly 60 to move rearwardly against the action of spring 72. Thus, as illustrated in FIG. 11, the jaws 18 first clamp the tissue 78, and thereafter draw the same within the ends of the cartridge assembly 20.

The cartridge assembly 20 is mounted to the forward end of the outer barrel 14. As best seen in FIGS. 1 and 2, the cartridge assembly 20 is provided with an outer barrel 80 having circumferential outwardly extending annular stop 82 (see also FIG. 15) which is engaged with the forward end 84 of the barrel 14. An extended key-shaped section 86 fits into a key slot 88, best seen in FIG. 5, formed in the end of barrel 14. Barrel 14 is provided with a spring hook 90 formed as an extension of a ring 92 for holding the annular stop 82 against the end of 84 of the barrel 14. The ring 92 is held from forward motion by means of a tab 94 extending into a hole 96 formed in the barrel 14.

Again referring to FIG. 2, the carrier or cartridge 20 is provided with an elongated hollow cylinder portion 98, which is free to rotate within the outer cylinder 80, but is prevented from lateral motion by means of a circumferential inwardly depending groove 100 in the cylinder 98 and one or more bosses or ridges 102 inwardly depending from the outer cylinder 80. The inner cylinder 98 is further provided with a pair of jaw extensions 104, 106 which engage the cam mechanism 22.

A plurality of pretied sutures 108, according to the invention, are mounted in a continuous helical groove 110 formed in the outer circumference of the forward end of cylinder 98. As best seen in FIG. 3, one of the loops 112 of the pretied suture 108 is engaged about one turn of the helix, while the other loop 114 thereof is engaged about an elongated pin 116 press fit within extension 86 of the outer cylinder 80. Thus, rotation of the inner cylinder 98 by means of the extension 104 and 106 in the clockwise direction, as seen in FIG. 3, will cause the sutures 108 to advance along the cartridge 20 and for each rotation one will be released from the end thereof.

For this purpose, a cam 118, best illustrated in FIG. 8, is provided. The cam is hollow to provide for the jaw rods 48 and 56. One end thereof is provided with a slot 120 for receiving the extension arms 104 and 106 of the cartridge 20. As shown in FIGS. 1 and 7, the cam is mounted within the outer barrel 14. The outwardly extending collar 122 of the cam 118 engages the inwardly extending collar 124 within the barrel 14 and prevents rearward motion of the cam 118. Forward motion is prevented by engagement against the cartridge 20. Cam 118, as best shown in FIG. 8, is provided with a continuous circumferential cam track 126, comprising a helical curved portion 128 encompassing approximately a 360° traverse of the cam 118 and a straight portion 130 connecting the two ends of the helical portion 128. The cam track 128 is engaged by a cam pin 132 mounted to inner barrel assembly 60. Thus, when trigger 24 is drawn back towards handle 16, pin 132 rides in the curved portion 128 of cam 118, causing cam 118 to turn clockwise, as seen in FIG. 8, one revolution, thus releasing the pretied suture 108' (FIG. 2) at the forward end of the cartridge 20, as best seen in FIG. 11. When the trigger 24 is released, cam pin 132 traverses the straight portion 130 of the cam track 126, readying the cam mechanism 22 for the next suture typing operation.

As best seen in FIGS. 11 through 13, pin 116 is provided with an end slot 134. Slot 134 receives hook 136 integral with hook arm 137 which is mounted to cutter arm 138 (FIGS. 1 and 7) at pivot pin 140. The entire cutter and hook operating assembly, generally indicated at 142, is mounted between brackets 144, and 145 which are integral with and extend below barrel 14. Pivot arms 146 and 148 are pivoted between brackets 144 and 145 at pivots 150 and 152. Cutter arm 138 is pivoted to pivot arms 146 and 148 at pivot pins 154 and 156 respectively. Cutter arm 138 is provided with slots 153, 155 and 157 for receiving hook arm 137, and pivot arms 146 and 148 which are of reduced thickness near pivots 140, 154 and 156. Trigger 28 is formed as an extension of hook arm 138.

Because the forward pivot arm 146 is longer than the rear pivot arm 148, when the trigger 28 is drawn rearwardly, the forward end of arm 138 will swing in a greater are downward and rearward, carrying the hook 136 along with it. The hook engages the lower loop 114 of the pretied suture, 108', as best seen in FIG. 12, and draws the ligature tight about the tissue 78. The hook 136 remains biased upwardly with respect to the forward end of cutter arm 138 through the action of downwardly biasing leaf spring 158, mounted to and between brackets 144 and 145, spring 158 biases a cutter trigger portion 160 of hook arm 137 clockwise about pivot 140. When the trigger 160 is pushed upwardly, hook 136 is caused to be drawn down into a slot 162 formed in the end of cutter arm 138, as best seen in FIG. 14. Slot 162 and hook 136 are provided with cooperating scissors-like sharp edges 164 and 166, which cut the lower loop 114 of the pretied suture 108, as best seen in FIG. 13. Hook arm 138 is biased upwardly by means of leaf spring 168.

It should be noted as best seen in FIGS. 11 through 13 that when loop 114 is pulled downwardly and rearwardly by hook 136, the forward end 170 of pin 116 which is curved upwards retains the knot portion 172 of the ligature 108 and pushes the same towards the bleeder tissue 78. Thus the ligature is tightened not only by pulling the loop 114 through the knot portion 172 but by actually pushing the knot portion against the bleeder 78.

Now referring to FIG. 6, each of the ligatures 108 is formed of a continuous loop of suture material 174 which may be gut or manmade absorbable material such as polyhydroxyacetic ester as disclosed in U.S. Pat. No. 3,225,766 and 3,297,033. The material 174 is preferably, but not necessarily, round in cross section. It is formed into a preformed suture as shown in FIG. 6D by first twisting it into the double loop configuration shown in FIG. 6A and then pulling a portion of the upper loop through the lower loop thus formed as shown in FIGS. 6B and 6C. The resulting pretied ligature 108 has two stable positions, those shown in FIGS. 6D and 6E. It is preferred that the sutures be mounted about the cartridge cylinder 98 and pin 116 as shown in FIG. 6D rather than as shown in FIG. 6E. It has been found that when it is mounted as shown in FIG. 6D the slip knot portion 172 thereof remains open as shown in FIG. 6D against the pin 116 of the cartridge 20 (FIG. 2) until the bleeder 78 begins resisting closure of the loop 112 when the ligature is nearly tight. This allows portion 176 of the ligature 108 to be drawn easily through the slip knot 172 until the final tightening. If the ligature is mounted as illustrated in FIG. 6E the portion 176 tends to interfere with the portion 178 during tightening and the knot 172 tends to become tight prematurely.

The repeating suture gun illustrated in FIGS. 1 through 13 is preferably manufactured of stainless steel which can be given a smooth surface so that all parts will operate easily without lubrication and can be conveniently sterilized. The cartridge 20 of FIG. 2 is preferably formed of Delrin or other plastic material which also can be sterilized. The pin 116 is stainless steel.

Summarizing the operation of the ligature gun, cartridge and ligatures illustrated in FIGS. 1 through 14 the surgeon holds the gun 12 in one hand by placing his thumb, third and fourth fingers about the handle 16. The middle finger operates the main trigger 24 and the index finger operates the hook trigger 28 and the cutter trigger 32.

When the surgeon pulls the trigger 24 towards the handle 16 with his middle finger, jaws 18 clamp about the bleeder and pull it inwardly into the hollow interior of cylinder 98 of cartridge 20. At the same time, pin 132 moving in helical cam track 128 rotates the cartridge one revolution, releasing the end pretied ligature 108' as seen in FIG. 11. The surgeon then pulls trigger 28 with his index finger drawing the hook 136 and cutter arm 138 downward and rearward as seen in FIG. 12. This pulls portion 176 of pretied ligature 108 as seen in FIG. 6D through slip knot portion 172. At the same time, pin 116 holds knot portion 172 open and in effect pushes it against bleeder 78 (FIG. 12) and the slip knot 172 is drawn tight. The amount of tightness is controlled by the surgeon in accordance with the amount of force applied to trigger 28. The surgeon then pushes his index finger slightly upward, engaging cutter trigger 32 which causes hook 136 to pass through opening 162 in cutter bar 138, thus cutting loop 114. When trigger 24 is released jaws 18 move forward and open, releasing the ligatured bleeder 78.

Now referring to FIG. 15, the entire mechanism may be conveniently disassembled for cleaning, as shown. Note that the cam 118 may be removed from the outer barrel 14 through the front of barrel 14 and that the inner barrel assembly 60 is removed by pulling it out of the rear of barrel 14 after barrel 14 has been disassembled from handle 16. The cartridge 20 is preferably supplied with pretied ligatures and the cartridge assembly sterilized. Thus, a plurality of cartridges may be made available for use in a single operation.

An alternative embodiment of the invention is illustrated in FIGS. 16 through 22. In this embodiment, the ligature cartridge 200 has an integral cam 202. This allows the repeating ligature gun, generally indicated at 204, to be cleaned without disassembly. Furthermore, the cam 202 being of plastic material provides a smoother action when it is being rotated by pin 206.

As seen in FIG. 17 in its unactuated position hook 208 is spaced from the end of cartridge pin 210. When the hook trigger 212 is operated, hook 208 is recessed in an opening 214 in the end of pin 210 to engage the lower loop 216 of preformed ligature 218. The ligature 218 is then drawn tight against pin 210 as shown in FIG. 21, and when trigger 212 is released the lower loop 216 of the ligature 218 is allowed to escape through the opening between the end of the hook 208 and the pin 210. Thus, the lower loop 216 need not be cut.

Another advantage of the embodiment shown in FIGS. 16 through 22 is that the hook trigger 212 is recessed within the jaws trigger 220. Note particularly and referring to FIGS. 16 and 17, that the repeating ligature gun 204 is provided with a handle 222 to which are mounted a pair of elongated support bars 224 and 226. Upper gripper jaw 228 is formed integrally on the end of an elongated shaft 230 which is half round at its forward end, and of circular cross section at its rearward end. This rod-like portion extends through opening 232 in handle 222, and is fixed to a trigger assembly 234 by pin 236 (FIG. 18).

Trigger assembly 234 is slidably mounted on bars 224 and 226 and is forwardly biased by springs 238 and 240. Arm 242 integral with trigger assembly 234 mounts pin 206 which engages cam track 244 of cam 202 as illustrated in FIG. 17. Cam track 244 is the same shape as cam track 126 illustrated in FIG. 8. Trigger 220 is pivotally mounted to trigger assembly 234 at pin 248, as best seen in FIG. 19. Slot 250 is formed in trigger 220 to receive hook trigger 212 as also seen in FIG. 19. Trigger 220 is normally biased in the clockwise direction about pin 248 due to springs 238–240 and the engagement of the forward upper edge 252 thereof with the end of cam 202. This causes a wishbone connection, generally indicated at 254, to a push lower jaw operating half round bar 256 rearwardly to open a lower jaw 258 which is pivoted to upper jaw actuating bar 230 at pivot 260 and to lower jaw actuating bar 256 at pivot 262.

A barrel assembly 264 is mounted to the forward end of support rods 224 and 226. Barrel assembly 264 comprises an inwardly depending annular stop 266 (best seen in FIG. 18) and a spring-like retaining clip 268. Clip 268 fits into a recess 270 in outer cylinder portion 272 of cartridge 200 and prevents rotation or forward motion thereof when it is inserted in barrel assembly 264.

As best seen in FIG. 16, cartridge 200 comprises a hollow cylindrical portion 274 having a helical track 276 and a rearward extension forcing cam 202. Outwardly extending annular collar 278 of portion 274 fits between stop 266 and outer cylinder 272 when the cartridge is mounted in barrel assembly 264 to prevent forward or rearward motion thereof. Outer cylinder 272 is provided with an integrally depending detent projection 280 which cooperates with inwardly depending annular depression 282 in cylinder 274 to keep the cartridge assembled. Metal rod 210 is press fit within outer cylinder 272 which preferably is of Delrin or other sterilizable plastic material as is inner cylinder 274.

The pretied or preformed ligatures 218 are mounted on the cartridge 200 in the manner described with reference to previous embodiments. That is, they may be the preformed sutures shown in FIG. 24 and as illustrated in FIG. 17 through 22 or they may be the form illustrated in FIG. 6D.

Hook 208 is mounted on elongated hook rod 284 and is slidable within strap 286 formed on hook guide arm 290. The rearward end 291 of hook guide arm 290 is pivotally mounted within recess 293 in handle extension 294 on pivot pin 292, as best seen in FIG. 20. Abutment 295 formed on handle extension 294, as best seen in FIG. 18, acts as a stop to rearward travel of trigger assembly 234.

The end of hook rod 284 is formed into a T-shaped extension 296 which is retained in spring 298 mounted to the lower end of handle extension 294 (FIGS. 18 and 20). Spring 298 biases hook 208 forwardly, as best seen in FIG. 17.

When trigger 220 is drawn rearward, as best seen in FIGS. 16 and 18, to cause the jaws 228 and 258 to grip the bleeder 78 and to pull it within the end of cartridge 200, the rearward upper edge 300 of trigger 220 pushes the T-shaped portion 296 of hook rod 284 rearward, causing the hook end to recess within the recess 214 in cartridge bar 210, as shown in FIG. 18. Simultaneously, pin 206 has traversed the helical portion of cam track 244 to rotate cam 202 (and thus helix 276) one revolution releasing the forwardmost preformed ligature 218, as shown in FIG. 18.

Hook trigger 212 is integrally formed on hook guide 290. Hook guide 290 has an opening 306 in the end therein for guiding hook 208 in its forward and rearward motion into and out of engagement with the recess 214 in pin 210 of cartridge 200. Hook guide 290 is biases clockwise aboutt is mounting pivot 292 by means of leaf spring 308 mounted to barrel assembly 264 at yoke 310. When trigger 212 is pulled, hook 208 and hook guide 290 move together counterclockwise about mounting pin 292 to tighten the ligature 218 about the bleeder 78. Hook 208 pulls the lower loop 216 and pin 210 holds the closure portion 312, as best seen in FIG. 21. As previously stated, when trigger 220 is released, the ligature may be disengaged from the gun without cutting, as illustrated in FIG. 22.

Now referring to FIG. 23, in a modified suture gun according to the invention the hook actuating trigger 316 is mounted forward of the jaws actuating trigger 220 and is slidably engaged about hook guide bar 318 by means of yokes 320 and 322 integral therewith. Guide bar 318 is biased clockwise about pivot 292 (FIG. 16) by means of leaf spring 324 mounted to modified yoke 326 integral with barrel assembly 264. Trigger 316 is normally biased forward by trigger 220 pushing against stop 328 mounted on trigger 316. Trigger 316 is pulled after trigger 220 has already been pulled, as previously described. Trigger 316 slides until a stop abutment 328 contacts trigger 220. Guide bar 318 is drawn counterclockwise about pivot 292 through the contact of inclined plane portion 327 of trigger slide assembly 316 with pin 325. Guide bar 318 brings hook rod 284 along with it since the hook bar is held within yoke 330. This modification provides increased leverage on the hook bar 284 through the action of the forwardly mounted sliding trigger 316.

The ligature gun illustrated in FIGS. 16 through 23 is preferably formed of stainless steel for the reasons stated with reference to the earlier described embodiment of the invention.

Now referring to FIGS. 24 and 24A and 24C, an alternative form of preformed ligature 218 according to the invention (also illustrated in FIGS. 17, 18, 21 and 22) comprises an endless loop of suture material 400 which may be collagen (gut) or the previously described synthetic material. Two pluralities of ratchet-like ridges 402 and 404 are formed on opposite sides of loop 400. An enveloping collar-like closure 312 is provided with cooperating pawl-like teeth 408 and 410 formed therein so that the collar 312 may be pushed towards the upper loop 412 or the upper loop 412 constricted by pulling on the lower loop 314. The closure 312 may have a pair of slits 412 and 414 formed therein to add to its resilience when traversing the ratchet teeth 402 and 404.

It will be apparent that it is absolutely necessary for the pin 210 of the cartridge 200 to engage the closure portion 312 and hold the same while the hook 208 engages the lower loop 216 (as shown in FIG. 21), since otherwise there would be no force between the loop 400 of suture material and closure 312. However, it is possible to make a closure which would act exactly like the loop of suture material formed into a double loop with a slipknot therebetween, as illustrated in FIG. 6D. This can be done by forming the continuous loop 400 and the closure 312 as an integral unit and providing only one side of the loop 400 with ratchet teeth which side can then be pulled through the closure 312 while the closure is held fixed to the other side of the continuous loop 400 about the bleeder. Other forms of molded plastic fasteners having integral closures such as now used to affix tags, tie bundles, wires and the like and sold under the Trademark "Secur-A-Tie" by Dennison Manufacturing Company may also be employed without departing from the scope of the invention.

Preformed ligatures of the general type illustrated in FIGS. 24 and 24A, B, and C may be applied by hand as illustrated in FIGS. 25 through 29. Referring to FIGS. 25, bleeder 300 has been clamped by hemostat 302 in the usual manner. A molded plastic ligature generally indicated at 304 comprises a large loop 306 which is large enough to pass over the hemostat 302. The loop 306 has a ratchet-like outer surface 308 formed of a plurality of pawl-like teeth 310. An elongated extension 312 ends in a finger engaging loop 314. The collar-like closure 316 is also provided with an elongated extension 318 ending in a finger engaging loop 320.

As best seen in FIG. 27, after the enlarged ligature loop 306 has been placed down about the bleeder 300, the two finger engaging loops 314 and 320 are engaged by the surgeon's fingers 322 and 324 and pulled to pull the closure 316 along the ligature loop 306 down to tight engagement about and to close the bleeder 300, as best seen in FIGS. 26. Thereafter, as shown in FIG. 26, the surgeon cuts off the elongated extensions 312 and 318 (FIG. 25) to leave the cut ends 326 and 328.

Referring to FIG. 28, the closure 316 may be provided with openings 330 and 332 (see also FIG. 26) to facilitate elastic deformation along the ratchet-like teeth 310.

Alternatively, as illustrated in FIG. 29, only the ligature loop 306 is provided with an elongated extension 312 and a finger engaging loop 314. In this case, an elongated stick 334 has an eyelet 336 mounted thereon which may or may not be provided with a narrow slot 338 for admitting the loop 306. Alternatively, the finger engaging loop 314 can be slid through the eyelet followed by the elongated extension 312. After the loop 306 is engaged about the bleeder 300, the eyelet 338 is pressed against closure 340 to slide it along the ratchet-like teeth 310 and close the loop to seal the bleeder 300. The surgeon holds the stick 334 in one hand 342 while engaging the finger engaging loop 314 with a finger 344 on the other hand.

An alternative form of loop ratchet and closure is illustrated in FIGS. 30 through 33. In this case the closure 346 is formed of plastic material having elastic memory so that it tends to form the circular shape illustrated in FIG. 31. In this case it fits snugly about elongated flat portions 348 and 350 on the ligature loop 352, and the ratchet-like teeth 354 and 356 prevent movement of the closure 346 in the upward direction of FIG. 30; however, the loop may be pushed axially downward to slip across teeth 358 and 360 as illustrated in FIG. 32. This deforms the loop 346 as illustrated in FIG. 33. The loop may be provided with an elongated extension 362 as illustrated in FIGS. 31 and 33 so that the ligature may be applied in the manner illustrated in FIG. 27 or it may be applied by means of an eyelet-like pusher as illustrated in FIG. 29.

I have thus provided preformed ligatures for bleeders and methods of applying such ligatures which may be employed to tie any number of bleeders during an operating procedure. These ligatures may be hand applied and such may be the most efficacious procedure for deep bleeders in inaccessible operating fields or they may be applied by use of my repeating ligature guns and multiligature cartridges in large numbers merely by changing presterilized cartridges of preformed ligatures.

It will thus be seen that the objects set forth above, among those made apparent from the preceding description, are efficiently attained and since certain changes may be made in the above articles and constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described my invention, what I claim as new and desire to secure by Letters Patent is:

1. A one piece ligature comprising a seamless ring of suture material twisted and tied into two loops divided by a slipknot such that by pulling on one loop or by spreading one loop open the other may be constricted.

2. A surgical ligature comprising a seamless ring of suture material having ratchet-like formations thereon and an elongated extension terminating in a finger loop into which a human finger may be placed, a closure of suture material engageable with said ring, said closure cooperating with said ratchet-like formations whereby said closure may be moved along said ring in only one direction to close a loop formed therein by said closure whereby by pulling in opposite directions on said closure and said fiinger loop, tissue in said loop formed by said closure may be ligated, and an elongated means having an eyelet-like member mounted thereto through which the elongated extension and seamless ring of material may be pulled to force said closure means therealong to close one end of said seamless ring of material.

3. A ligature as defined in claim 2 wherein said closure means is provided with ratchet-like formations cooperating with the ratchet-like formations on said seamless ring of material to provide motion of such closure means in only one direction along said seamless ring of material.

4. A ligature as defined in claim 2 wherein said eyelet-like member is provided with a slot-like opening therein.

5. A surgical ligature comprising a seamless ring of suture material having ratchet-like formations thereon and an elongated extension terminating in a first finger loop into which a human finger may be placed, a closure of suture material engageable with said ring, said closure cooperating with said ratchet-like formations whereby said closure may be moved along said ring in only one direction to close a loop formed therein by said closure, said closure having an elongated extension terminating in a second finger loop into which a human finger may be placed whereby by pulling in opposite directions on said finger loops, tissue in said loop formed by said closure may be ligated.

6. A ligature as defined in claim 5 further defined in that there are two sets of ratchet-like formations on opposite halves of said seamless ring of material and two pawl-like formations on opposite sides of said closure means.

7. A ligature as defined in claim 5 wherein said closure means is formed of material having an elastic memory, and it is deformed from its normal shape when passing over said ratchet-like formations.

8. A ligature as defined in claim 7 wherein spaces are provided between the individual ratchet-like formations, at least equal in axial width to the axial width of said closure means.

* * * * *

UNITED STATES PATENT AND TRADEMARK OFFICE
CERTIFICATE OF CORRECTION

PATENT NO. : 3,985,138

DATED : October 12, 1976

INVENTOR(S) : Robert K. Jarvik

It is certified that error appears in the above-identified patent and that said Letters Patent are hereby corrected as shown below:

Column 1, Line 10 -- delete "18" and substitute therefore --17--;
Column 1, Lines 47, 48 -- delete "determined" and substitute therefore --determining--;
Column 1, line 57 -- delete "beed" and substitute therefore --been;
Column 3, Line 1 -- delete first "and" and substitute therefore --are--;
Column 4, Line 49 -- delete "injected" and substitute therefore --injection--;
Column 4, Line 57 -- delete "as" and substitute therefore --a--;
Column 6, Line 24 -- delete "extensions" and substitute therefore --extension--;
Column 6, Line 51 -- insert --a-- after "having";
Column 7, Line 41 -- delete "typing" and substitute therefore --tying--;
Column 7, Line 60 -- delete "are" and substitute therefore --arc--;
Column 10, Line 59-- delete "biases" and substitute therefore --biased--;
Column 10, Line 59 -- delete "aboutt" and substitute therefore --about--;
Column 10, Line 59 -- delete "is" and substitute therefore --its--;
Column 12, Line 39 -- delete "of" and substitute therefore --in--.

Signed and Sealed this

Third Day of May 1977

[SEAL]

Attest:

RUTH C. MASON
*Attesting Officer*

C. MARSHALL DANN
*Commissioner of Patents and Trademarks*